United States Patent [19]

Morgan

[11] Patent Number: 4,916,251

[45] Date of Patent: Apr. 10, 1990

[54] CYANOISOALKYLATION OF HYDROXY SUBSTITUTED ARYL COMPOUNDS USING KETONES

[75] Inventor: Ted A. Morgan, Midland, Mich.

[73] Assignee: The Dow Chemical Company, Midland, Mich.

[21] Appl. No.: 223

[22] Filed: Jan. 2, 1987

[51] Int. Cl.$^4$ ............................................ C07C 121/75
[52] U.S. Cl. .................................................... 558/332
[58] Field of Search ........................................ 558/332

[56] References Cited

U.S. PATENT DOCUMENTS

| | | |
|---|---|---|
| 3,886,283 | 5/1975 | Dory et al. . |
| 4,388,250 | 6/1983 | Farber et al. . |
| 4,405,528 | 9/1983 | Everly et al. . |
| 4,459,224 | 7/1984 | van der Weerdt et al. . |
| 4,483,800 | 11/1984 | Everly et al. . |
| 4,485,051 | 11/1984 | Everly et al. . |
| 4,487,722 | 12/1984 | Everly et al. . |
| 4,536,343 | 8/1985 | Ramachandran . |

OTHER PUBLICATIONS

Cotton "Advanced Inorganic Chem." 2nd ed. 1966 p. 312.

A. Johnsson, *Act. Chem. Scand.*, 8, 1203–10 (1954).

*Primary Examiner*—Alan Siegel
*Attorney, Agent, or Firm*—Paula Sanders Ruhr

[57] ABSTRACT

A method for cyanoisoalkylating phenols or other hydroxy-substituted aryl compounds, which may have up to two substitutents ortho or para to the hydroxy moiety, comprising reacting a molar excess of phenol or aryl compound with a ketone in the presence of cyanide ion and hydroxide ion at an elevated temperature.

Compounds, such as 4-(1-cyano-1-methylethyl)phenol, produced via this method are useful as chemical intermediates in the preparation of polyurethanes, epoxy resins and pharmaceutical and agricultural products.

20 Claims, No Drawings

CYANOISOALKYLATION OF HYDROXY SUBSTITUTED ARYL COMPOUNDS USING KETONES

BACKGROUND OF THE INVENTION

This invention relates to processes for the preparation of aryl compounds substituted with a cyanoisoalkyl moiety and a hydroxy moiety wherein both the cyanoisoalkyl and hydroxy moieties are substituents on the same ring and particularly to processes for the preparation of cyanoisoalkylphenols.

Cyanoisoalkylphenols have numerous applications an are particularly useful as chemical intermediates in the preparation of polyurethanes, epoxy resins and pharmaceutical and agricultural products.

Methods are known for preparing cyanoalkylphenols and, more particularly, cyanoisoalkylphenols. One process for the preparation of cyanoisoalkylphenols involves a complex multi-step synthesis whereby a dimethylbenzylhalide is converted to the cyanide, ring nitrated, hydrogenated, and then subjected to diazotization. See A. Johnsson, *Act. Chem. Scand.*, 8, 1203–10 (1954). The problem with this process is that it is a low-yielding, multi-step, time-consuming, and uneconomical route.

Another process for the preparation of cyanoalkylphenols is disclosed in U.S. Pat. No. 4,405,528. This is a process for the synthesis of 4-($\alpha$-alkyl-$\alpha$-cyanomethyl)-2,6-disubstituted phenol by reacting a 2,6-disubstituted phenol with a Friedel-Crafts addition agent in the presence of a Friedel-Crafts catalyst such as aluminum chloride to form the corresponding 4-($\alpha$-alkyl-$\alpha$-oxomethyl)-2,6-disubstituted phenol, reducing the 4-($\alpha$-alkyl-$\alpha$-oxomethyl)-2,6-disubstituted phenol to form the corresponding 4-($\alpha$-alkyl-$\alpha$-hydroxymethyl)-2,6-disubstituted phenol and thereafter reacting the 4-($\alpha$-alkyl-$\alpha$-hydroxymethyl)-2,6-disubstituted phenol with an alkali metal cyanide or an alkaline earth metal cyanide to form the desired 4-($\alpha$-alkyl-$\alpha$-cyanomethyl)-2,6-disubstituted phenol.

A process for the preparation of 4-($\alpha$-hydrocarbyl-$\alpha$-cyanomethyl)-2,6-disubstituted phenols is disclosed in U.S. Pat. No. 4,483,800 wherein said cyanomethylphenol is prepared by reacting a disubstituted phenol with an aldehyde and an alkali metal cyanide or an alkaline earth metal cyanide in a suitable solvent.

What is needed is a versatile one-step process for utilizing inexpensive starting materials to produce cyanoisoalkylphenols and other hydroxy and cyanoisoalkyl substituted aryl compounds.

SUMMARY OF THE INVENTION

The present invention is a process for the preparation of hydroxy and cyanoisoalkyl substituted aryl compounds which avoids many of the problems associated with prior methods as well as provides greater versatility than the previous methods. The process of the present invention comprises bringing together a hydroxy substituted aryl compound which is unsubstituted in at least one of the positions ortho or para to the hydroxy moiety, a ketone, cyanide ion and sufficient hydroxide ion under reaction conditions sufficient to produce an aryl compound substituted with a hydroxy moiety and a cyanoisoalkyl group which is ortho or para to the hydroxy moiety.

DETAILED DESCRIPTION OF ILLUSTRATIVE EMBODIMENTS

The aryl compounds useful in the process of this invention are substituted by a hydroxy moiety and may include one or more additional, essentially nonreactive substituents. Further, these compounds are unsubstituted in at least one position ortho or para to the hydroxy moiety.

It is preferred to use phenols as reactants in the process of this invention. The phenols may be substituted in any two of the positions ortho and para to the hydroxy moiety and are unsubstituted in the third position.

Preferred phenols correspond to the following general formula:

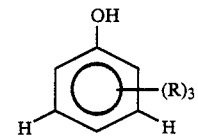

wherein each R is independently hydrogen, $C_{1-20}$ alkyl or $C_{3-10}$ carbocyclic, alkyl and carbocyclic in each instance being unsubstituted or substituted by one or more substituents selected from halo, e.g., chloro and bromo: alkyl, e.g., methyl, ethyl, propyl and others having up to 6 carbons: aryl, e.g., phenyl: alkoxy, e.g , methoxy: nitro: amino: sulfo: cyano: acyl and the like with the proviso that none of these is reactive with the ketones utilized in the process of the present invention and with the further proviso that at least one R group ortho or para to the hydroxy group is hydrogen.

In a more preferred embodiment of this invention, the R group para to the hydroxy group is hydrogen and the R groups ortho to the hydroxy moiety are each independently hydrogen or $C_{1-6}$ alkyl. It is even more preferred that the R groups ortho to the hydroxy group are each independently hydrogen or methyl and it is most preferred that R in each occurrence is hydrogen.

The ketones useful in this invention include aliphatic and cyclic ketones. Preferred ketones useful in the present process correspond to the following general formula:

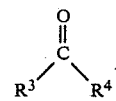

wherein $R^3$ and $R^4$ are independently $C_{1-20}$ straight or branched chain alkyl, alkyl in each instance being unsubstituted or substituted by one or more substituents selected from halo e.g., chloro and bromo: alkyl, e.g., methyl, ethyl, propyl and others having up to 6 carbons: aryl, e.g., phenyl: alkoxy, e.g., methoxy: nitro; amino: sulfo: cyano: acyl and the like with the proviso that none of these substituents is reactive in the process of the present invention. In an even more preferred embodiment of this invention, $R^3$ and $R^4$ are each independently $C_{1-6}$ alkyl and in the most preferred embodiment, $R^3$ and $R^4$ are each methyl. Preferred cyclic ketones useful in this invention are the $C_{3-10}$ cyclic ketones. A more preferred cyclic ketone is cyclohexanone.

The most preferred embodiment of this invention constitutes heating a mixture of phenol, acetone, cyanide ion, and hydroxide ion to about 150° C. and maintaining that temperature for about 18 hours. The product, 4-(1-cyano-1-methylethyl)phenol, is recovered by recrystallization. About 100 percent of the ketone is converted to products with about 60 percent of the product being 4-(1-cyano-1-methylethyl)phenol.

The process of the present invention can be carried out using any molar ratio of the ketone to the hydroxy-substituted aryl compound that will allow the reaction to proceed. A preferred range of proportions of the ketone to the aryl compound on a molar basis is about 1:1 to about 1:15. A more preferred range is about 1:2 to about 1:10, and the most preferred ratio is about 1:5.

Cyanide ion as used herein means a cyanide ion in salt form and specifically excludes hydrogen cyanide. Suitable forms of cyanide ion include lithium cyanide, tetraalkylammonium cyanide, sodium cyanide and potassium cyanide. Preferred forms of cyanide ion include sodium cyanide and potassium cyanide, with sodium cyanide being most preferred.

The process of this invention can be carried out using any molar ratio of cyanide ion to the hydroxy-substituted aryl compound that will provide sufficient cyanide ion to form the cyanoisoalkylated product. A preferred molar ratio of cyanide ion to the aryl compound is typically in the range of from about 1:1 to about 1:15, with about 1:2 to about 1:10 being more preferred. The most preferred molar ratio is about 1:5.

Hydroxide ion as used herein means a hydroxide ion which is highly ionized or dissociated. Preferred forms of hydroxide ion include lithium hydroxide, tetraalkylammonium hydroxide, sodium hydroxide and potassium hydroxide. More preferred forms of hydroxide ion include sodium hydroxide and potassium hydroxide, with sodium hydroxide being most preferred.

The process of this invention can be carried out using any molar ratio of hydroxide ion to the hydroxy-substituted aryl compound that will provide sufficient hydroxide ion for the reaction to proceed. The preferred molar ratio of hydroxide ion to the aryl compound is in the range from about 1:1 to about 1:15, with about 1:2 to 1:5 being more preferred. The most preferred molar ratio is about 2:5.

The process of the present invention can be carried out at any temperature at which the reaction will proceed. Preferably, the reaction mixture is elevated to a temperature in the range from about 120° C. to about 200° C., with the range from about 140° C. to about 160° C. being most preferred. The process is carried out for a period of time which will allow substantial conversion of the starting material. Preferred reaction times are in the range from about 10 to about 40 hours, with the range from about 10 to about 20 hours being most preferred. The process of the present invention can be carried out at any pressure at which the reaction will proceed. Preferred pressure ranges extend up to about 50 psi ($3.45 \times 10^5$ Pascals). The more preferred pressure is that which is generated by the reactants themselves, i.e., autogeneous pressure, in a closed vessel.

The present process may be carried out neat or a solvent may be employed. Any solvent which is inert and will dissolve the starting materials can be employed in the present process. Aprotic solvents such as N,N-dimethylformamide, dimethylsulfoxide, formamide, glyme, diglyme, glycol, hexamethylphosphoramide, or N-methylpyrrolidone are preferred with N,N-dimethylformamide being the most preferred solvent. When a solvent is employed, it is used in amounts that will dissolve a sufficient amount of reactants to facilitate the reaction, preferably in amounts in the range from about 50 to about 75 weight percent based on the weight of the reaction medium. However, in the most preferred embodiment of this invention, no solvent is employed.

Conversions typically obtained in the practice of the process of this invention are in the range from about 80 to 100 percent based on the ketone. Preferred conversions are about 90 to 100 percent. It is most preferred that conversions are about 100 percent. The selectivity to the desired cyanoisoalkylated product is typically in the range from about 25 to 60 percent based on the ketone. The preferred selectivity to the desired cyanoisoalkylated product is about 60 percent.

Typical cyanoisoalkylphenols readily prepared by the process of the present invention include 4-(1-cyano-1-methylethyl)phenol, 2-(1-cyano-1-methylethyl)phenol, 4-(2-(2-cyanobutyl))phenol, 2-(2-(2-cyanobutyl))phenol, 4-(2-(2-cyanopentyl))phenol, 2-(2-(2-cyanopentyl))phenol, 4-(3-(3-cyanopentyl))phenol, 2-(3-(3-cyanopentyl))phenol, 4-(2-(2-cyanohexyl))phenol, 2-(2-(2-cyanohexyl))phenol, 4-(3-(3-cyanohexyl))phenol, 2-(3-(3-cyanohexyl))phenol, 4-(1-(1-cyanocyclohexyl))phenol, 2-(1-(1-cyanocyclohexyl))phenol, 4-(1-(1-cyanocyclopentyl))phenol, 2-(1-(1-cyanocyclopentyl))phenol, 4-(1-(1-cyanocycloheptyl))phenol, and 2-(1-(1-cyanocycloheptyl))phenol, with 4-(1-cyano-1-methylethyl)phenol, 4-(2-(2-cyanobutyl))phenol, 4-(2-(2-cyanopentyl))phenol, 4-(3-(3-cyanopentyl))phenol, 4-(2-(2-cyanohexyl))phenol, 4-(3-(3-cyanohexyl))phenol, 4-(1-(1-cyanocyclohexyl))phenol, 4-(1-(1-cyanocyclopentyl))phenol, and 4-(1-(1-cyanocycloheptyl))phenol being preferred. The most preferred cyanoisoalkylphenol is 4-(1-cyano-1-methylethyl)phenol.

SPECIFIC EMBODIMENTS

The following example further illustrates the invention and should not be construed as limiting its scope. All parts and percentages are by weight unless otherwise indicated.

Example 1 — Preparation of
4-(1-Cyano-1-Methylethyl)Phenol

To a 300 ml Parr stainless steel bomb equipped with a Magnadrive stirrer are added 47 g (0.5 mole) of phenol, 5.8 g (0.1 mole) of acetone, 5.4 g (0.11 mole) of sodium cyanide, and 8.8 g (0.22 mole) of sodium hydroxide. The reaction mixture is heated at 150° C. for about 18 hours. After cooling, the reaction mixture is neutralized with aqueous HCl and then extracted with $CHCl_3$ three times using 300 ml of $CHCl_3$ each time. The combined $CHCl_3$ extract is dried over $MgSO_4$, filtered, and then concentrated to give a brown oil. The phenol is removed by vacuum distillation to give a brown solid. This crude is dissolved in $CHCl_3$, filtered through silica gel, and then recrystallized from hot 1:1 $CHCl_3$-hexane solution to give 7 g of a colorless solid with a melting point of 99° C.-101° C. The product is identified by standard nuclear magnetic resonance techniques, gas chromatography, mass spectroscopy and infrared spectroscopy.

WHAT IS CLAIMED IS:

1. A process to produce a cyanoisoalkylated, hydroxy aryl compound comprising bringing together a hydroxy substituted aryl compound which is unsubstituted in at least one of the positions ortho or para to the hydroxy moiety, a ketone, cyanide ion and sufficient hydroxide ion under reaction conditions sufficient to produce an aryl compound substituted with a hydroxy moiety and a cyanoisoalkyl group which is ortho or para to the hydroxy moiety.

2. The process of claim 1 wherein the hydroxy substituted aryl compound is a phenol unsubstituted in at least one of the positions ortho or para to the hydroxy moiety.

3. The process of claim 2 wherein the phenol corresponds to the formula:

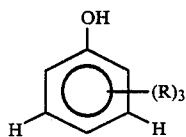

wherein R is independently hydrogen, $C_{1-20}$ alkyl or $C_{3-10}$ carbocyclic, alkyl and carbocyclic in each instance being unsubstituted or substituted by one or more substituents selected from halo, alkyl, aryl, alkoxy, nitro, amino, sulfo, cyano, acyl and the like with the proviso that none of these is reactive with the ketones utilized in the process of the present invention and R is ortho or para to the hydroxy moiety with the further proviso that at least one R group ortho or para to the hydroxy moiety is hydrogen.

4. The process of claim 3 wherein the ketone is a $C_{3-10}$ cycloketone or a ketone corresponding to the formula

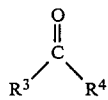

wherein $R^3$ and $R^4$ are independently $C_{1-20}$ straight-chained or branched alkyl, alkyl in each instance being unsubstituted or substituted by one or more substituents selected from halo, alkyl, aryl, alkoxy, nitro, amino, sulfo, cyano, acyl and the like with the proviso that none of these substituents is reactive in the process of the present invention.

5. The process of claim 4 wherein the cycloketone is cyclohexanone.

6. The process of claim 4 wherein the ketone is acetone.

7. The process of claim 6 wherein R in each occurrence is hydrogen.

8. The process of claim 7 wherein the cyanide ion is in the form of sodium cyanide or potassium cyanide.

9. The process of claim 8 wherein the hydroxide ion is in the form of sodium hydroxide or potassium hydroxide.

10. The process of claim 4 wherein the molar ratio of the ketone to the phenol is between about 1:2 and 1:10.

11. The process of claim 10 wherein the molar ratio of the ketone to the phenol is about 1:5.

12. The process of claim 2 wherein the molar ratio of the cyanide ion to the phenol is between about 1:2 and about 1:10.

13. The process of claim 12 wherein the molar ratio of the cyanide ion to the phenol is about 1:5.

14. The process of claim 2 wherein the molar ratio of the hydroxide ion to the phenol is between about 1:2 and about 1:10.

15. The process of claim 14 wherein the molar ratio of the hydroxide ion to the phenol is about 2:5.

16. The process of claim 1 wherein the reaction is carried out at a temperature between about 120° C. and about 200° C.

17. The process of claim 16 wherein the temperature is between about 140° C. and about 160° C.

18. The process of claim 9 wherein the cyanide ion is in the form of sodium cyanide and the hydroxide ion is in the form of sodium hydroxide.

19. The process of claim 1 wherein no solvent medium is employed.

20. A process for the preparation of 4-(1-cyano-1-methylethyl)phenol comprising heating a solventless mixture of phenol, acetone, cyanide ion, and hydroxide ion to about 150° C., maintaining that temperature for about 18 hours and recovering the 4-(1-cyano-1-methylethyl)phenol in a yield of about 60 percent.

* * * * *